United States Patent [19]
Aoki et al.

[11] Patent Number: 6,068,845
[45] Date of Patent: May 30, 2000

[54] INHIBITION OF ABNORMAL ACCUMULATION OF EXTRA-CELLULAR MATRICES

[75] Inventors: Hiroe Aoki; Eijiro Hara; Tetsuji Hirao, all of Yokohama, Japan

[73] Assignee: Institute for Advanced Skin Research Inc., Yokohama, Japan

[21] Appl. No.: 08/877,351

[22] Filed: Jun. 17, 1997

[30] Foreign Application Priority Data

Jun. 19, 1996 [JP] Japan .................................. 8-177180
Mar. 31, 1997 [JP] Japan .................................. 9-094495

[51] Int. Cl.$^7$ .................................................. A61K 7/26
[52] U.S. Cl. .................................. 424/195.1; 424/78.05; 424/78.06; 424/407; 514/886
[58] Field of Search ............... 424/195.1, 78.05, 424/78.06, 407; 514/886

[56] References Cited

U.S. PATENT DOCUMENTS

| | | | |
|---|---|---|---|
| 5,066,669 | 11/1991 | Iwasaki et al. | 514/449 |
| 5,658,933 | 8/1997 | Weidmann et al. | 514/350 |
| 5,725,804 | 3/1998 | Yen | 252/314 |

FOREIGN PATENT DOCUMENTS

| | | |
|---|---|---|
| 2 037 M | 9/1963 | France . |
| 403161423 | 7/1991 | Japan . |

OTHER PUBLICATIONS

Border et al, J. Clin. Invest., 90; 1–7, Jul. 1992.
Ignotz et al, J. Biol. Chem., 261(9), 4337–4345, Mar. 25, 1986.
Roberts et al, PNAS, U.S.A. 83, 4167–4171, Jun. 1986.
Patent Abstracts of Japan, vol. 014, No. 318, Publication No. 02111710, Publication Date Apr. 24, 1990.
Database WPI, Section Ch, Week 8732, Derwent Publications Ltd., London, GB; Class B04, AN 87–224316 XP002065791 & JP 62 148 426 A *abstract*.
Patent Abstracts of Japan, vol. 018, No. 307, Jun. 13, 1994 & JP 06 065087 A, Mar. 8, 1994 * abstract *.
Database WPI, Section Ch, Week 9439, Derwent Publications Ltd., London, GB; Class B04, AN 94–313628 XP002065804 & JP 06 239 758 A * abstract *.
Patent Abstracts of Japan, vol. 017, No. 195, Apr. 16, 1993 & JP 04 342519 A, Nov. 30, 1992 * abstract *.
Patent Abstracts of Japan, vol. 013, No. 278, Jun. 26, 1989 & JP 01 075422 A, Mar. 22, 1989 * abstract *.

*Primary Examiner*—Thurman K. Page
*Assistant Examiner*—Lakshmi Channavajjala
*Attorney, Agent, or Firm*—Wenderoth, Lind & Ponack, L.L.P.

[57] ABSTRACT

This invention provides a pharmaceutical preparation or cosmetic, and a method for effectively inhibiting the abnormal accumulation of extra-cellular matrices. In addition, a method for preventing or treating a disease resulting from the abnormal accumulation of extra-cellular matrices is also disclosed. The pharmaceutical preparation or cosmetic contains as an effective ingredient at least one substance selected from the group consisting of the extract of a plant belonging to the genus Artemisia, the genus Forsythia, the genus Sophorak the genus Pheutn the genus GI rhiza, the genus Arctium, the genus Anemarrhena, the genus Aralia, the genus Anelicia, the genus Akebia or the genus Atractylodes, the genus Akebia or the genus Atractilodes, malotilate, 2,2'-dipyridyl and o-phenanthroline.

9 Claims, No Drawings

INHIBITION OF ABNORMAL ACCUMULATION OF EXTRA-CELLULAR MATRICES

BACKGROUND OF THE INVENTION

This invention relates to the inhibition of the abnormal accumulation of extracellular matrices; and more specifically, the invention relates to a method and cosmetic or pharmaceutical preparation for inhibiting the abnormal accumulation of extracellular matrices in dermal cells, thereby preventing or treating a disease associated with the abnormal accumulation, and the use of a certain substance for preparing such a preparation.

The transforming growth factor β (TGF-β) was found as a factor accelerating the transformation of cells, and thereafter, has been ascertained to act as a growth-inhibiting factor or the like on many cells. TGF-β is known to exhibit many activities for example, it is considered that TGF-β acts on fibroblasts, etc., accelerating the production of extracellular matrices such as collagen, and causing the abnormal accumulation of the extracellular matrices, which is a cause of various diseases.

As diseases which may be associated with such abnormal accumulation of extracellular matrices, there are mentiond, for example, fibrosis-like cancer, pulmonary fibrosis, arteriosclerosis, posterior cardiac infarction, glomerular nephritis, cardiac fibrosis, restenosis after angioplasty, renal interstitial fibrosis, keloid, scleroderma, hypertrophic scar, etc. For the purpose of treating these diseases, there have been proposed agents causing the inhibition of the synthesis of collagen, for example, peptide derivatives obtained by using the inhibition of protocollagen proline hydroxylase activity as an indication (Japanese Patent Publication No. 29740/ 1977 and Japanese Patent Publication No. 20298/ 1982), serine derivatives obtained by using the acceleration of the production of procollagenase as an indication (Japanese Patent Publication No. 79645/1993), etc.

However, extracellular matrices, on one hand, have relation to the regulation of physiological functions such as the adhesion, movement, growth, differentiation, etc. of cells, and thus substances screened using the inhibition of collagen synthesis as an indication cannot always be regarded as ones suitable for living bodies. Therefore, as substances for the prophylaxis or treatment of the above diseases inhibiting the extracellular matrix-producing activity of TGF-β itself, there have been proposed anti-TGF-β antibodies, platelet-derived growth factors (PDGF), etc.

However, it cannot always be said that a safe and effective prophylactic and treating method is established particularly against skin fibrosis such as keloid, hypertrophic scar or scleroderma, among diseases which can be regarded as ones caused by the abnormal accumulation of extracellular matrices in the skin.

Thus, the object of this invention lies in providing an agent for inhibiting the abnormal accumulation of extracellular matrices which can safely be used particularly for the prophylaxis and treatment of skin fibrosis.

The present inventors directed their attention to the phenomenon that in dermal fibroblasts activated with TGF-β, the production of extracellular matrices is abnormally accelerated. The inhibition of the production (or accumulation) of the matrices in such an extracellular matrix-producing system seems to reproduce the actual physical functions more faithfully and make it possible to screen substances having effectiveness and high safety, compared with the above cases, for example the case where the inhibition of collagen synthesis is merely used as an indication.

Thus, we screened agents using as an indicator the inhibitory activity on the abnormal production of extracellular matrices in dermal fibroblasts activated with TGF-β. As a result we found that certain plant extracts and compounds, belonging to categories different from that to which substances have been screened using the inhibition of collagen synthesis as an indicator, have excellent inhibitory activity against the abnormal production of extracellular matrices.

Among these substances, there are included lntin-koo extract (for example, Japanese Laid-open Patent Publication No. 300812/1992 and Japanese Laid-open Patent Publication No. 65087/1994), *Forsythia suspensa* $V_{AHL}$, extract (for example, Japanese Laid-open Patent Publication No. 152325/1984, Japanese Laid-open Patent Publication No. 207023/1990 and Japanese Laid-open Patent Publication No. 16525/1994), *Sophora flavescens* $A_{ITON}$. or *Sophora anaustifolia* extract (for example, Japanese Laid-open Patent Publication No. 104005/ 1985, Japanese Laid-open Patent Publication No. 90131/ 1989, Japanese Laid-open Patent Publication No. 128934/ 1989, Japanese Laid-open Patent Publication No. 111710/ 1990, Japanese Laid-open Patent Publication No. 346917/ 1992, Japanese Laid-open Patent Publication No. 229955/ 1993 and Japanese Laid-open Patent Publication No. 25 336418/1994), and *Rheum Dalmatum* L. extract (for example, Japanese Laid-open Patent Publication No. 42485/ 1985, Japanese Laid-open Patent Publication No. 10006/ 1987, Japanese Laid-open Patent Publication No. 93710/ 1991, Japanese Laid-open Patent Publication No. 243834/ 1992, Japanese Laid-open Patent Publication No. 97653/ 1993 and Japanese Laid-open Patent Publication No. 207776/1995), These substances are crude drugs each exhibiting inhibitory activity on tyrosinase, lipase, hyaluronidase or the like or bacteriostatic activity and being used as a component of dermal external preparations for whitening action, for the prevention of acne vulgaris or for hair tonicity. However, there is no disclosure in past technical literatures including these official patent publication teaching that the above extracts can be used for the inhibition of the abnormal production of extracellular matrices in dermal fibroblasts, and there is no disclosure therein suggesting such use, either.

SUMMARY OF THE INVENTION

Thus, according to this invention provides, an agent for inhibiting the abnormal accumulation of extracellular matrices which comprises at least one substance selected from the group consisting of the extract of a plant belonging to the genus Artemisia, the genus Forsythia, the genus Sophora, the genus Rheum, the genus Glycyrrhiza, the genus Arctium, the genus Anemarrhena, the genus Aralia, the genus Angelica, the genus Akebia or the genus Atractylodes, malotilate, 2,2'-dipyridyl and o-phenanthroline in an amount effective to inhibit the abnormal accumulation of extracellular matrices, and a suitable amount of pharmaceutically or cosmetically acceptable vehicle(s). Further, as the invention of another embodiment, there is also provided a method for preventing or treating a disease associated with the abnormal accumulation of extracellular matrices which comprises applying at least one of the above substances in an amount effective to inhibit the abnormal accumulation of extracellular matrices, to a subject liable to suffer or suffering from a disease associated with the abnormal accumulation of extracellular matrices.

Further, as the invention of still another embodiment, there is also provided the use of at least one of the above substances in an amount effective to inhibit the abnormal accumulation of extracellular matrices, for preparing a preparation for preventing or treating a disease associated with the abnormal accumulation of extracellular matrices.

Further, as the invention of still another embodiment, there is also provided a process for preparing a preparation for inhibiting the abnormal accumulation of extracellular matrices which comprises mixing or kneading at least one of the above substances in an amount effective to inhibit the abnormal accumulation of extracellular matrices, with a suitable amount of pharmaceutically or cosmetically acceptable vehicle(s), and thereby solubilizing or homogenizing the substance.

According to the invention, the natural production of extracellular matrices in the subject is not adversely affected, and the invention contributes for the prophylaxis or treatment of various diseases caused by the abnormal accumulation of extracellular matrices.

DETAILED DESCRIPTION OF THE INVENTION

Substances used in the invention can, more specifically, be used advantageously for inhibiting the abnormal production of extracellular matrices in dermal fibroblasts activated with TGF-β. Thus as a preferred embodiment of the invention, there is provided an agent for inhibiting the abnormal accumulation of extracellular matrices particularly in the case where the abnormal accumulation occurs in the dermal cells. However, so long as the object of the invention can be attained, agents for inhibiting the abnormal accumulation of extracellular matrices in other organs or tissues are not to be excluded.

Further, plants belonging to the genus Artemisia, the genus Forsythia, the genus Sophora, the genus Rheum, the genus Glycyrrhiza, the genus Arctium, the genus Anemarrhena, the genus Aralia, the genus Angelica, the genus Akebia and the genus Atractylodes according to the invention can be used regardless of their species, habitats, etc. so long as their extracts exert actions and effects which the invention aims at.

For example, as plants belonging to the genus Artemisia, there can be mentioned *Artemisia capillaris* $T_{HUNB}$. (Chinese name: lntin-koo) and *Artemisia absinthium* L. and their natural mutants, etc. but *Artemisia capillaris* $T_{HUNB}$. or its mutant is preferably used. The extracts of these plants are prepared from the entire herbs mainly including corolla tubes. As plants belonging to the genus Forsythia, there can be mentioned *Forsythia suspensa* $V_{AHL}$., *Forsythia viridissima* $L_{IND}$. and *Forsythia koreana* $N_{AKAI}$. and their natural mutants, etc., and as their extracts, those prepared mainly from their achenes are preferred. As plants belonging to the genus Sophora, there can be mentioned *Sophora flavescens* $A_{ITON}$, (Chinese name: Kujin), *Sophora japonica* L.) and their natural mutants, etc., and particularly an extract derived from the roots of the former can be used preferably. As plants belonging to the genus Rheum, there can be mentioned *Rheum palmatum* L., *Rheum officinale* $B_{AIL}$. and *Rheum tanzuticum* $M_{AXIM}$. and their natural mutants, etc., and their extracts are mainly prepared from their roots and stems.

As plants belonging to the genus Glycyrrhiza, there can be mentioned *Glycyrrhiza glabra* L. var. glandulifera Regel et Herder, *Glycyrrhiza glabra* L., *Glycyrrhiza uralensis* $F_{ISHER}$ et De Candolle, *Glycyrrhiza glabra* L. var. violacea Boiss., etc., and particularly an extract derived from the roots of *Glycyrrhiza glabra* L. var. Elandulifera Regel et Herder (Kanzoo) can be used preferably. As plants belonging to the genus rctium, there can be mentioned *Arctium lappa* L. and its natural mutants, etc., and particularly extracts derived from the fruits of them (Goboosi) can be used preferably.

As plants belonging to the genus Anemarrhena, here can be mentioned *Anemarrhena asphodeloides* $B_{UNGE}$. and its natural mutants, etc., and particularly an extract derived from the roots and stem of *Anemarrhena asohodeloides* $B_{UNGE}$. (zhimu) can be used preferably. As plants belonging to the genus Aralia, there can be mentioned *Aralia cordata* Thunb. and *Aralia glabra* Matsum and their natural mutants, etc., and particularly an extract derived from the roots and stem of *Aralia cordata* Thunb. (Dokkatu) can be used preferably. As plants belonging to the genus Angelica, there can be mentioned *Angelica pubescens* Maxin and its natural mutants, etc., and particularly an extract derived from the roots of *Angelica Dubescens* Maxin (Dokkatu) can be used preferably.

As plants belonging to the genus Akebia, there can be mentioned *Akebia auinata* Decne., *Akebia trifoliata* $K_{OIDZ}$. and *Akebia pentaphvyla* Makino. and their natural mutants, etc., and particularly extracts derived from the stems of them (mutong) can be used preferably. As plants belonging to the genus Atractylodes, there can be mentioned *Atractylodes iaponica* Koidz. and *Atractylodes lancea* DC. and its natural mutants, etc., and particularly an extract derived from the roots and stem of *Atractylodes lancea* DC. (soozyutu) can be used preferably.

The term natural mutants is intended to include mutants bred for the purpose of cultivation.

Each of the above extracts can be obtained by, if necessary, drying and grinding the part of the herbal body which was mentioned as the object of extraction, and extracting the resultant matter with water (including hot water) or an organic solvent (for example, petroleum ether, cyclohexane, toluene, carbon tetrachloride, dichioromethane, chloroform, diethyl ether, diisopropyl ether, ethyl acetate, butanol, n-propanol, ethanol, methanol, polyethylene glycol, propylene glycol, pyridine, etc.) or a mixed solvent of two or more of them, usually at 3 to 70° C. Such an extract can be used as such or after it is diluted, concentrated or dried.

According to the invention, besides the above plant extracts, o-phenanthroline and 2,2-dipyridyl whose use as a chelating agent is known, respectively, and malotilate whose inhibitory activity on the development of hepatic fibrogenesis is known can each be used as an active ingredient of an agent which inhibits the abnormal accumulation of extracellular matrices. Particularly as to malotilate, it is contemplated to target the abnormal accumulation of extracellular matrices which occurs in dermal cells.

In the invention, it is also contemplated to use the inhibitory agent of the invention for the prophylaxis and treatment of diseases associated with the abnormal accumulation of extracellular matrices in various organs or tissues, for example, diseases such as fibrosis-like cancer, pulmonary fibrosis and arteriosclerosis, but, particularly, it is strongly contemplated to use it for the prophylaxis or treatment of skin fibrosis such as keloid, scieroderma and hypertrophic scar.

Thus the inhibitory agent of the invention can be provided as a preparation wherein at least one of the above extracts and compounds is combined, if necessary, with pharmaceutically or cosmetically acceptable, commonly used vehicle (s), for example, diluent(s) or excipient(s) such as filler(s), extender(s), binder(s), humectant(s), disintegrant(s), disintegration inhibitor(s), surfactant(s) and lubricant(s). Various dosage forms can be selected as pharmaceutical preparations in accordance with their therapeutic purposes, and as representative examples thereof there can be mentioned tablets, pills, powders, liquids, suspension syrups, emulsions, granules, capsules, suppositories, injections (liquids, suspensions, etc.), etc. Further, according to the invention, it is preferred to provide the inhibitory agent of the invention, particularly among the above, in dosage forms commonly used as dermal external (or transdermic) preparations or cosmetics, and as representative examples thereof, there can be mentioned liquids, emulsions, creams, sticks, gels, lotions, packs, etc.

Auxiliaries usable at the time of preparing preferred dermal external preparations are not limited, but within such a range that the effects of the invention are not spoiled, there can be compounded various components generally used in cosmetics, quasi-medical drugs, medical drugs, etc., for example, aqueous components, oily components, humectants, thickeners, corrosives, antioxidants, ultraviolet absorbers, powdery components, perfumes, colorants, pharmaceuticals, etc. For example, there can be mentioned hydrocarbons such as solid or liquid paraffins, crystal oils, ceresine, ozokerite and montan wax, silicone oils, vegetable or animal fats and oils and waxes such as olive oil, earth wax, carnauba wax and lanolin, fatty acids or their esters such as stearic acid, palmitic acid, oleic acid, glycerol stearate esters, glycerol monooleate ester, isopropyl myristate esters, isopropyl stearate esters, esters of branched fatty acids with monohydric alcohols or polyhydric alcohols, alcohols such as ethyl alcohol, isopropyl alcohol, cetyl alcohol and palmityl alcohol, polyhydric alcohols such as glycols, glycerol and sorbitol or their esters, and surfactants such as nonionic surfactants, anionic surfactants and cationic surfactants.

Further, there can also be used polysaccharides, cholesterols, placenta extract, derivatives of glycyrrhizin, derivatives of glycyrrhetinic acid, tocopherol and its derivatives, ascorbic acid and its derivatives, kojic acid and its derivatives, hydroquinones, flavonoids, retinol, hinokitiol, indomethacin and, antioxidants or ultraviolet absorbers such as butylhydroxytoluene. In addition, there can also appropriately be compounded sequestering agents such as disodium edetate, trisodium edetate, sodium citrate, sodium polyphosphate, sodium metaphosphate and gluconic acid, pharmaceuticals such as caffeine, tannin, verapamil, tranexamic acid and its derivatives, glabridin, extract of the fruit of *Pyracantha fortuneana* with hot water, tocopherol acetate, and whitening agents such as vitamin C, ascorbic acid phosphate ester magnesium salt, ascorbic acid glucoside, arbutin and kojic acid, saccharides such as glucose, fructose, mannose, sucrose and trehalose, etc.

The amount of effective ingredient(s) which the above preparation can contain cannot be specified because the optimum amount thereof varies depending on the kind of the disease intended to be prevented or treated, the degree of the symptom and the kind of the effective ingredient(s) used. When the preparation is a dermal external preparation and the extract of any of plants as described later is used, it is possible to regulate the amount to 1 $\mu$g or more preferably 0.1 mg to 1 mg per g of the preparation. When the preparation is a dermal external preparation and o-phenanthroline, 2,2'-dipyridyl or malotilate is used, it is possible to regulate the amount to 0.01 % by weight or more, preferably 1 % by weight to 10 % by weight in the preparation. As to the administration route of the dermal external preparation, application to topical skin which may be or is affected with a disease whose prophylaxis or treatment is contemplated can be mentioned as a specific example.

The preparation according to the invention can be prepared, if necessary, by solubilizing or homogenizing the above substance having an inhibitory activity on the abnormal accumulation of extracellular matrices in pharmaceutically or cosmetically acceptable vehicle(s). This solubilization or homogenization can be carried out using instrument (s) and technique(s) commonly used in the art.

The dose of the resultant preparation can appropriately be increased or decreased depending on direction for use, the age, sex and other conditions of the patient, the degree of the disease, etc., but it is necessary that the dose should be enough to attain a pharmacologically effective level in the animal to which the preparation was administered.

When the inhibitory agent according to the invention thus prepared and applied is used, the natural production of extracellular matrices is not substantially adversely affected, but the abnormal production of extracellular matrices can be inhibited significantly.

The invention is described in more detail below by specific examples, but it is not intended to limit the invention to these examples.

Preparation Examples of Plant Extracts

EXAMPLE 1

Intin-koo Extract

20 Volumes of ethanol was added to 10 g of dried Artemisia capillaris $T_{HUNB}$. (Chinese name: Intin-koo), the mixture was ultrasonicated at ordinary temperature for 1 hour and then shaken for 30 minutes to carry out extraction, and an extract was obtained by filtration. The extract was concentrated and dried to give 0.62 g of an Intin-koo extract.

EXAMPLE 2

*Forsythia suspensa* $V_{AHL}$. Extract

20 Volumes of purified water was added to 10 g of dried *Forsythia suspensa* $V_{AHL}$., the mixture was ultrasonicated at ordinary temperature for 1 hour and then shaken for 30 minutes to carry out extraction, and an extraction filtrate was obtained by filtration. This was concentrated and dried to give 0.85 g of a *Forsythia suspensa* $V_{AHL}$. extract.

EXAMPLE 3

*Sophora flavescens* $A_{ITON}$. Extract

20 Volumes of purified water was added to 10 g of dried *Sophora flavescens* $A_{ITON}$. (Chinese name: Kujin), the mixture was refluxed at 80° C. for 2 hours to carry out extraction, and an extraction filtrate was obtained by filtration. This was concentrated and dried to give 1.47 g of a *Sophora flavescens* $A_{ITON}$. extract.

EXAMPLE 4

*Rheum Dalmatum* L. Extract

20 Volumes of ethanol was added to 10 g of dried *Rheum palmatum* L., the mixture was refluxed at 80° C. for 2 hours to carry out extraction, and an extraction filtrate was obtained by filtration. This was concentrated and dried to give 1.89 g of a *Rheum palmatum* L. extract.

EXAMPLE 5

*Glycyrrhiza glabra* L. var. glandulifera Regel et Herder Extract

20 Volumes of purified water was added to 10 g of dried Glycyrrhiza glabra L. var. Elandulifera Regel et Herder, the mixture was ultrasonicated at ordinary temperature for 1 hour and then shaken for 30 minutes to carry out extraction, and an extraction filtrate was obtained by filtration. This was concentrated and dried to give 1.15 g of a *Glycyrrhiza alabra* L. var. *glandulifera* Regel et Herder extract.

EXAMPLE 6

Goboosi Extract

20 Volumes of purified water was added to 10 g of dried Goboosi, the mixture was ultrasonicated at ordinary temperature for 1 hour and then shaken for 30 minutes to carry out extraction, and an extraction filtrate was obtained by filtration. This was concentrated and dried to give 0.72 g of Goboosi extract.

EXAMPLE 7

Goboosi Extract with Ethanol

20 Volumes of ethanol was added to 10 g of dried Goboosi, the mixture was ultrasonicated at ordinary temperature for 1 hour and then shaken for 30 minutes to carry out extraction, and an extraction filtrate was obtained by filtration. This was concentrated and dried to give 0.57 g of a Goboosi extract.

EXAMPLE 8

Zhimu Extract

20 Volumes of purified water was added to 10 g of dried zhimu, the mixture was ultrasonicated at ordinary temperature for 1 hour and then shaken for 30 minutes to carry out extraction, and an extraction filtrate was obtained by filtration. This was concentrated and dried to give 0.59 g of a zhimu extract.

EXAMPLE 9

Dokkatu Extract

20 Volumes of purified water was added to 10 g of dried Dokkatu, the mixture was refluxed at 80° C. for 2 hours to carry out extraction, and an extraction filtrate was obtained by filtration. This was concentrated and dried to give 0.95 g of a Dokkatu extract.

EXAMPLE 10

Mutong Extract

20 Volumes of purified water was added to 10 g of dried mutong, the mixture was ultrasonicated at ordinary temperature for 1 hour and then shaken for 30 minutes to carry out extraction, and an extraction filtrate was obtained by filtration. This was concentrated and dried to give 1.03 g of a mutong extract.

EXAMPLE 11

Soozyutu Extract

20 Volumes of ethanol was added to 10 g of dried soozyutu, the mixture was ultrasonicated at ordinary temperature for 1 hour and then shaken for 30 minutes to carry out extraction, and an extraction filtrate was obtained by filtration. This was concentrated and dried to give 0.47 g of a soozyutu extract.

Inhibitory Test on the Production of Extracellular Matrices

Test Example 1

Inhibitory Activity on the Production of Extracellular Matrices with TGF-β Stimulation 1) Test Sample Test samples used were Intin-koo extract (Preparation example 1), Forsythia suspensa $V_{AHL}$. extract (Preparation example 2), Sophora flavescens $A_{ITON}$. extract (Preparation example 3), Rheum palmatum L. extract (Preparation example 4), Glycyrrhiza alabra L. var. glandulifera Regel et Herder extract (Preparation example 5), Goboosi extract with water (Preparation example 6), Goboosi extract with ethanol (Preparation example 7), zhimu extract (Preparation example 8), Dokkatu extract (Preparation example 9), mutong extract (Preparation example 10), soozyutu extract (Preparation example 11), o-phenanthroline (produced by Dojin Chemical Co.: special grade chemical), 2,2'-dipyridyl (produced by Aldrich Chemical Co.) and malotilate (extracted from Kantec tablet produced by Daiichi Pharmaceutical Co.).

2) Test Cell

Human newborn dermal fibroblasts (NB1RBG) (obtained from the Institute of Physical and Chemical Research) was subcultured in DMEM medium containing 10 % fetal bovine serum for provision to the test.

3) Test Method $2 \times 10^4$ NB1RBG cells per well were incubated in flat-bottomed 96-well microtiter plates containing 100 μl/well of each of DMEM media each containing 1 % fetal bovine serum and containing one of the test samples and TGF-β (5 ng/ml), at 37° C.-5 % $CO_2$ for 5 days. A group not containing any test sample or TGF-β was also prepared, and incubation thereof was carried out at the same time with the test groups. After the completion of the incubation, the flat-bottomed 96-well microtiter plates on which the adhered cells and the extracellular matrices were adhered were stained with the following two methods for evaluation, respectively.

(a) Staining With a Dye

First, the culture supernatants were removed, the wells were washed with phosphate-buffered physiological saline, 100 μl/well of 0.05 % Crystal Violet–20 % ethanol staining solution was added, and the mixtures were left alone at room temperature for 10 minutes. Then, the plates were washed with flowing water and air dried, the remaining Crystal Violet was dissolved with 100 μl/well of methanol, and the absorbance at O.D. 570–690 was measured by a plate reader. The inhibition percentages of the production of extracellular matrices in an unstimulating state and in a TGF-β-stimulating state were calculated according to the following equations.

The inhibition percentage of the production of extracellular matrices in an unstimulating state (%)

$$= \left(1 - \frac{B}{A}\right) \times 100$$

The inhibition percentage of the production of extracellular matrices in a TGF-β-stimulating state (%)

$$= \left(\frac{C-D}{C-A}\right) \times 100$$

A: The absorbance of a group containing only the solvent with which the test sample was prepared, and not containing TGF-β.

B: The absorbance of a group containing a test sample, but not containing TGF-β.

C: The absorbance of a group containing the solvent with which the test sample was prepared, and TGF-β.

D: The absorbance of a group containing a test sample and TGF-β.

(b) Staining with anti-collagen antibody

First, the culture supernatants were removed, the wells were washed with phosphate-buffered physiological saline, and fixation was carried out with methanol under ice cooling for 10 minutes. Then, blocking was made with milk protein solution, Block Ace (produced by DAINIPPON PHARMACEUTICAL CO.), and rabbit anti-human type I collagen antibody (produced by CHEMICON CO.), biotin-labeled anti-rabbit immunoglobulin (produced by Amersham CO.) and avidin-biotin-labeled peroxidase complex (produced by Amersham CO.) were successively reacted to enzyme-label the sedimented type I collagen. 100 μl/well of 0.1 M citric acid phosphate buffer (pH 4.0) containing 2.5 mM 2,2'-azino-bis(3-ethylbenzothia-zoline-6-sulfate) (produced by SIGMA CO.) and 0.015 % $H_2O_2$ was reacted therewith, and one hour later, absorbance at O.D. 415 was measured by a plate reader. The inhibition percetages of the type I collagen sedimentation in an unstimulating state and in a TGF-β-stimulating state were calculated according to the following equations.

The inhibition percentage of the production of extracellular matrices in an unstimulating state (%)

$$= \left(1 - \frac{F}{E}\right) \times 100$$

The inhibition percentage of the production of extracellular matrices in TGF-β-stimulating state (%)

$$= \left(\frac{G - H}{G - E}\right) \times 100$$

E: The absorbance of a group containing only the solvent with which the test sample was prepared, and not containing TGF-β.
F: The absorbance of a group containing a test sample, but not containing TGF-β.
G: The absorbance of a group containing the solvent with which the test sample was prepared, and TGF-β.
H: The absorbance of a group containing a test sample and TGF-β.

The test results are shown together in the following Table 1.

TABLE 1

Inhibitory activity on the extracellular matrices production of fibroblasts with TGF-β

| | | Inhibition percentage (%) of the extracellular matrices production | | | |
| | | Dye staining method | | Collagen staining method | |
| | Concen- | TGF-β Stimulation | | | |
| Test substance | ration | (−) | (+) | (−) | (+) |
| Sophora flavescens $A_{ITON}$- extract | 4 μg/ml | −7 | −3 | −5 | 0 |
| | 40 | 4 | 55 | −1 | 43 |
| | 400 | 38 | 99 | 57 | 95 |
| Forsythia suspensa $V_{AHL}$- extract | 4 | 11 | 5 | 0 | 0 |
| | 40 | 31 | 38 | −9 | 11 |
| | 400 | 27 | 81 | −25 | 30 |
| Intin-koo extract | 1 | 14 | 7 | 1 | 13 |
| | 10 | 16 | 15 | 0 | 32 |

TABLE 1-continued

Inhibitory activity on the extracellular matrices production of fibroblasts with TGF-β

| | | Inhibition percentage (%) of the extracellular matrices production | | | |
| | | Dye staining method | | Collagen staining method | |
| | Concen- | TGF-β Stimulation | | | |
| Test substance | ration | (−) | (+) | (−) | (+) |
| | 100 | 26 | 70 | −1 | 63 |
| Rheum palmatum L. extract | 1 | 6 | 5 | 8 | 13 |
| | 10 | 23 | 36 | 3 | 57 |
| | 100 | 4 | 69 | 17 | 97 |
| Malotilate | $1 \times 10^{-6}$ M | 21 | 18 | 9 | 20 |
| | $1 \times 10^{-5}$ | 23 | 53 | 6 | 68 |
| | $1 \times 10^{-4}$ | 20 | 92 | 7 | 98 |
| 2,2'-Dipyridyl | $1 \times 10^{-6}$ M | 5 | 7 | 10 | 14 |
| | $1 \times 10^{-5}$ | 25 | 7 | 15 | 30 |
| | $1 \times 10^{-4}$ | 44 | 84 | 18 | 77 |
| o-Phenanthroline | $1 \times 10^{-6}$ M | 7 | 1 | 11 | 27 |
| | $1 \times 10^{-5}$ | 0 | 86 | 16 | 90 |
| | $1 \times 10^{-4}$ | 0 | 95 | 20 | 100 |
| Glycyrrhiza glabra L. var. glandulifera Regel et Herder extract with water | 2 μg/ml | 8 | −10 | 5 | 6 |
| | 20 | 18 | 12 | 13 | 8 |
| | 200 | 6 | 95 | 6 | 86 |
| Goboosi extract with water | 2 | 9 | 15 | 0 | −3 |
| | 20 | 16 | 80 | −2 | 43 |
| | 200 | 94 | 96 | 80 | 91 |
| Goboosi extract with ethanol | 2 | 28 | 35 | 10 | 21 |
| | 20 | 12 | 97 | −6 | 98 |
| | 200 | 62 | 100 | 56 | 97 |
| Zhimu extract with water | 2 | −14 | 45 | 0 | 24 |
| | 20 | 34 | 95 | 11 | 100 |
| | 200 | 100 | 96 | 74 | 100 |
| Dokkatu extract with water | 2 | 12 | −15 | −1 | 0 |
| | 20 | 10 | 9 | −9 | 7 |
| | 200 | −3 | 95 | 14 | 87 |
| Mutong extract with water | 2 | 5 | 8 | 0 | 2 |
| | 20 | 25 | 72 | 6 | 45 |
| | 200 | 68 | 97 | 52 | 92 |
| Soozyutu extract with ethanol | 2 | 20 | 17 | −12 | 0 |
| | 20 | 19 | 20 | 0 | 5 |
| | 200 | 16 | 68 | 2 | 35 |

Test Example 2
Inhibitory Activity on the Production of Collagen in Dermal Fibrosis Model According to the method of Ichihara et al. (Hifu (Skin) volume 14, 217–226, 1972), inhibitory activity on a model of dermal fibrosis induced with bleomycin was investigated.
1) Test Samples
The same as above
2) Test Animal
Hos:hr-1 male hairless mice (5 weeks old) were used.
3) Test Method
10 mg/kg/day portions of bleomycin were intraperitoneally administered to the hairless mice for 10 successive days. 0.1 ml Portions of ethanol solutions or Vaseline ointments of the Sophora flavescens $A_{ITON}$- extraction, the Rheum palmatum L. extract, o-phenanthroline and malotilate were applied onto the back skins every day from the start of the test, respectively. 30 Days later from the start of the test, the back skins were excised. The amounts of collagen in the excised skins were assayed using hydroxyproline amount as an index. The assay of hydroxyproline amount was carried out according to the method of Kivirikko et al. (Analitical Biochemistry vol. 19, 249–255 (1967)).

The inhibition percentage of dermal fibrosis with bleomycin was caluculated according to the following equation.

Inhibition percentage of dermal fibrosis (%)

$$= \left(\frac{K-L}{K-J}\right) \times 100$$

J: Hydroxyproline amount in the untreated group
K: Hydroxyproline amount in the group of bleomycin administration+application of the base alone
L: Hydroxyproline amount in the group of bleomycin administration+application of the drug The test results are shown together in Table 2.

TABLE 2

Inhibitory effect on dermal fibrosis with bleomycin

|  | Hydroxyproline amount per weight of dried skin ($\mu$g/mg) | Inhibition percentage (%) |
| --- | --- | --- |
| Untreated group | 1.34 ± 0.12 | — |
| Bleomycin administration group | 1.85 ± 0.06 | — |
| Bleomycin administration + ethanol application group | 1.92 ± 0.11 | — |
| Bleomycin administration + 1% Kujin extract application group | 1.76 ± 0.30 | 27.6 |
| Bleomycin administration + 5% Kujin extract application group | 1.67 ± 0.27 | 43.1 |
| Bleomycin administration + 1% *Rheum palmatum* L. extract application group | 1.86 ± 0.15 | 10.3 |
| Bleomycin administration + 5% *Rheum palmatum* L. extract application group | 1.55 ± 0.19 | 63.8 |
| Bleomycin administration + 5% *Glycyrrhiza glabra* L. var. *glandulifera* Regel et Herder extract application group | 1.92 ± 0.23 | 44.4 |
| Bleomycin administration + 10% *Glycyrrhiza glabra* L. var. *glandulifera* Regel et Herder extract application group | 1.65 ± 0.18 | 81.9 |
| Bleomycin administration + 5% mutong extract application group | 1.88 ± 0.15 | 50.0 |
| Bleomycin administration + 10% mutong extract application group | 1.75 ± 0.20 | 68.1 |
| Bleomycin administration + 5% Dokkatu extract application group | 2.11 ± 0.14 | 18.1 |
| Bleomycin administration + 10% Dokkatu extract application group | 1.96 ± 0.16 | 38.9 |
| Bleomycin administration + Vaseline application group | 2.01 ± 0.13 | — |
| Bleomycin administration + 5% malotilate application group | 1.66 ± 0.25 | 52.2 |
| Bleomycin administration + 10% malotilate application group | 1.47 ± 0.19 | 80.6 |
| Bleomycin administration + 5% o-phenanthroline application group | 1.72 ± 0.16 | 43.3 |
| Bleomycin administration + 10% o-phenanthroline application group | 1.43 ± 0.10 | 86.6 |

It will be understood from Table 2 that the agents for inhibiting the abnormal accumulation of extracellular matrices according to the invention significantly inhibit dermal fibrosis with bleomycin.

Formulation Examples of Preparations (all the compounding amounts mean % by weight)

EXAMPLE 1

Cream

| A. Oily phase | |
| --- | --- |
| Stearic acid | 10.0% |
| Stearyl alcohol | 4.0 |
| Glycerol monostearate ester | 8.0 |
| Evitamin E acetate | 0.5 |
| Perfume | 0.4 |
| Ethylparaben | 0.1 |
| Butylparaben | 0.1 |
| Propylparaben | 0.1 |
| B. Aqueous phase | |
| Intin-koo extract (derived from Preparation example 1) | 5.0 |

-continued

| 1,3-Butylene glycol | 10.0 |
| --- | --- |
| Propylene glycol | 8.0 |
| Glycerol | 2.0 |
| Potassium hydroxide | 0.4 |
| Purified water | Remainder |

(Preparation Process)

The respective components of the oily phase A. were successively mixed and dissolved to give an oily phase. The lntin-koo extract was dissolved in 1,3-buty lene glycol, and the remaining components were successively dissolved to give the aqueous phase B. The oily phase and the aqueous phase were heated to 70° C., respectively, to complete dissolution, and the oily phase was added to the aqueous phase, and the mixture was emulsified by an emulsifier. The emulsion was cooled using a heat exchanger to give a cream.

EXAMPLE 2

Cream

| A. Oily phase | |
| --- | --- |
| Cetanol | 4.0% |
| Vaseline | 7.0 |
| Isopropyl myristate | 8.0 |
| Squarane | 12.0 |
| Polydimethylsiloxane | 3.0 |
| Glycerol monostearate ester | 2.2 |
| POE(20) sorbitan monostearate | 2.8 |
| Glycyrrhetinic acid stearate | 0.02 |
| Ethylparaben | 0.1 |
| Butylparaben | 0.1 |
| B. Aqueous phase | |
| *Forsythia suspensa* $V_{AHL}$. extract (derived Preparation example 2) | 0.1 |
| 1,3-Butylene glycol | 7.0 |
| Phenoxyethanol | 0.2 |
| Ascorbic acid phosphate ester magnesium salt | 1.0 |
| Purified water | Remainder |

(Preparation Process)

A cream was obtained in the same manner as in Formulation example 1 of a preparation.

EXAMPLE 3

Lotion

| A. Alcohol phase | |
| --- | --- |
| Ethanol | 20.0% |
| POE(60) hardened castor oil | 3.0 |
| Octyl paramethoxycinnamate | 1.0 |
| Perfume | 0.3 |
| B. Aqueous phase | |
| *Sophora flavescens* $A_{ITON}$. extract (derived from Preparation example 3) | 5.0 |
| Dipropylene glycol | 5.0 |
| 1,3-Butylene glycol | 10.0 |
| Polyethylene glycol 400 | 10.0 |
| Triethanolamine | 5.0 |
| Purified water | Remainder |

(Preparation Process)

POE(60) hardened castor oil, octyl paramethoxycinnamate and the perfume were dissolved in ethanol (Alcohol phase A.). On the other hand, the *Sophora flavescens* $A_{ITON}$. extract was dissolved in 1,3-butylene glycol, and purified water and the other polyhydric alcohols and so on were added, followed by sufficient dissolution (Aqueous phase B.). The alcohol phase was added to the aqueous phase, and the mixture was sufficiently mixed to give a lotion.

EXAMPLE 4

Pack

| A. Alcohol phase | |
| --- | --- |
| 95% Ethanol | 10.0 |
| POE (15) oleyl alcohol ether | 2.0 |
| Ethylparaben | 0.2 |
| Butylparaben | 0.1 |
| Perfume | 0.1 |
| B. Aqueous phase | |
| *Rheum palmatum* L. extract (derived from Preparation example 4) | 0.5 |
| Polyvinyl alcohol | 12.0 |
| Glycerol | 3.0 |
| Polyethylene glycol | 1.0 |
| Purified water | Remainder |

(Preparation Process)

The respective components of the alcohol phase A. were mixed at room temperature to give an alcohol phase. Then, the respective components of the aqeous phase B. were mixed at 80° C. to give an aqueous phase, and it was cooled to 50° C. The alcohol phase was added to the aqueous phase, and the mixture was uniformly mixed and left to cool, whereby a pack was obtained.

EXAMPLE 5

Cream

| A. Oily phase | |
| --- | --- |
| Stearyl alcohol | 7.0 |
| Stearic acid | 2.0 |
| Lanolin | 2.0 |
| Squarane | 5.0 |
| 2-Octyldodecyl alcohol | 6.0 |
| POE(25) Cetyl alcohol ether | 3.0 |
| Glycerol monostearate ester | 2.0 |
| Malotilate (the same as in Test example 1) | 1.0 |
| Ethylparaben | 1.0 |
| B. Aqueous phase | |
| Propylene glycol | 10.0 |
| Purified water | Remainder |

(Preparation Process)

Propylene glycol was added to purified water, and the mixture was heated and maintained at 70° C. (aqueous phase). The respective components of the oily phase A. were successively mixed, dissolved with heating and maintained at 70° C. (oily phase). The oily phase was added to the aqueous phase, and the mixture was subjected to preparatory emulfication, uniformly emulsified by a homomixer and cooled to 30° C. under adequate stirring to give a cream.

EXAMPLE 6

Cream

| A. Oily phase | |
| --- | --- |
| o-Phenanthroline (the same as in Test example 1) | 0.1 |
| Stearic acid | 2.0 |
| Stearyl alcohol | 7.0 |
| Hydrogenated lanolin | 2.0 |

| -continued | |
|---|---|
| Squarane | 5.0 |
| 2-Octyldodecyl alcohol | 6.0 |
| EPOE(25) Cetyl alcohol ether | 3.0 |
| Glycerol monostearate ester | 2.0 |
| Ethylparaben | 5.0 |
| Perfume | 0.1 |
| B. Aqueous phase | |
| Propylene glycol | 5.0 |
| Purified water | Remainder |

(Preparation Process)

A cream was obtained in the same manner as in Formulation example 5 of a preparation.

EXAMPLE 7
Cream

| | |
|---|---|
| Stearic acid | 5.0 |
| Stearyl alcohol | 4.0 |
| Butyl stearate ester | 8.0 |
| Glycerol monostearate ester | 2.0 |
| 2,2'-Dipyridyl | 0.5 |
| (the same as in Test example 1) | |
| Propylene glycol | 10.0 |
| Glycerol | 4.0 |
| Potassium hydroxide | 0.2 |
| Antiseptic, antioxidant | Appropriate amount |
| Perfume | Appropriate amount |
| Deionized water | Remainder |

(Preparation Process)

Propylene glycol and potassium hydroxide were added to deionized water to give a solution, and it was heated and maintained at 70° C. (aqueous phase). The other components were mixed and melted with heating and maintained at 70° C. (oily phase). The oily phase was added gradually to the aqueous phase, and after the completion of the addition, the mixture was maintained at that temperature for a while to cause reaction. Then, the mixture was uniformly emulsified by a homomixer and cooled to 30° C. under adequate stirring.

EXAMPLE 8
Cream

| A. Oily phase | |
|---|---|
| Cetanol | 4.0 |
| Vaseline | 7.0 |
| Isopropyl myristate | 8.0 |
| Squarane | 12.0 |
| Polydimethylsiloxane | 3.0 |
| Glycerol monostearate ester | 2.2 |
| POE(20) sorbitan monostearate | 2.8 |
| Stearate glycyrrhetinate | 0.02 |

| -continued | |
|---|---|
| Ethylparaben | 0.1 |
| Butylparaben | 0.1 |
| o-Phenanthroline | 0.5 |
| B. Aqueous phase | |
| Intin-koo extract | 1.0 |
| (Preparation example 1) | |
| Sophora flavescens $A_{ITON}$. | 1.0 |
| (Preparation example 3) | |
| 1,3-Butylene glycol | 7.0 |
| Phenoxyethanol | 0.2 |
| L-Ascorbic acid phosphate ester magnesium | 3.0 |
| Purified water | Remainder |

(Preparation Process)

A cream was obtained in the same manner as in Formulation example 1 of a preparation.

What is claim:

1. A method of inhibiting the abnormal accumulation of extracellular matrices in a disease process, which comprises administering a substance comprising an extract of a plant, said plant belonging to the genus Sophora, the genus said substance being present in an amount effective to inhibit the abnormal accumulation of extracellular matrices in the disease process, to a subject liable to suffer or suffering from a disease process associated with the abnormal accumulation of extracellular matrices.

2. The method according to claim 1, wherein the substance is administered transcutaneously through the subject's skin.

3. The method according to claim 1, wherein the disease is one caused by an abnormal production of TGF-$\beta$.

4. The method according to claim 1, wherein the abnormal accumulation of extracellular matrices is mainly caused by the abnormal production of collagen.

5. The method according to claim 1, wherein the disease is skin fibrosis.

6. The method according to claim 1, wherein the plant belonging to the genus Sophora is Sophora flavescens $A_{ITON}$., or a natural mutant thereof.

7. A method of preventing or treating skin fibrosis, which comprises topically applying to the skin of a subject in need thereof a substance comprising an extract of a plant, said plant belonging to the genus Sophora, said substance being applied in an amount effective to inhibit the abnormal accumulation of extracellular matrices to thereby treat or prevent skin fibrosis.

8. The method according to claim 1 wherein the plant belonging to the genus Sophora is Sophora flavescens $A_{ITON}$., or a natural mutant thereof.

9. The method according to claim 7, wherein the substance is contained in a composition including a pharmaceutically or cosmetically acceptable vehicle.

\* \* \* \* \*